United States Patent
Rousseau

(10) Patent No.: US 6,575,988 B2
(45) Date of Patent: Jun. 10, 2003

(54) DEPLOYMENT APPARATUS FOR SUPPLE SURGICAL MATERIALS

(75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/855,872

(22) Filed: May 15, 2001

(65) Prior Publication Data

US 2002/0173804 A1 Nov. 21, 2002

(51) Int. Cl.$^7$ .............................................. A61B 17/08
(52) U.S. Cl. ..................................................... 606/151
(58) Field of Search ................................ 606/151, 213, 606/215, 157; 128/899, 898, 887; 623/11.11, 1.23

(56) References Cited

U.S. PATENT DOCUMENTS

| | | | |
|---|---|---|---|
| 5,116,357 A | 5/1992 | Eberbach | |
| 5,122,155 A | 6/1992 | Eberbach | |
| 5,141,515 A | 8/1992 | Eberbach | |
| 5,258,000 A | 11/1993 | Gianturco | |
| 5,279,539 A | 1/1994 | Bohan et al. | |
| 5,350,399 A * | 9/1994 | Erlebacher et al. | 128/899 |
| 5,366,460 A * | 11/1994 | Eberbach | 128/887 |
| 5,370,650 A | 12/1994 | Tovey et al. | |
| 5,397,331 A | 3/1995 | Himpens et al. | |
| 5,634,931 A | 6/1997 | Kugel | |
| 5,695,525 A | 12/1997 | Mulhauser et al. | |
| 5,766,246 A | 6/1998 | Mulhauser et al. | |
| 5,769,864 A | 6/1998 | Brown | |
| 5,824,082 A | 10/1998 | Brown | |
| 5,916,225 A | 6/1999 | Kugel | |
| 5,957,939 A * | 9/1999 | Heaven et al. | 606/151 |
| D416,327 S | 11/1999 | Kugel | |
| 6,171,318 B1 | 1/2001 | Kugel et al. | |
| 6,174,320 B1 | 1/2001 | Kugel et al. | |
| 6,176,863 B1 | 1/2001 | Kugel et al. | |
| 6,193,731 B1 * | 2/2001 | Oppelt et al. | 604/13 |

FOREIGN PATENT DOCUMENTS

EP 0583964 2/1994

\* cited by examiner

*Primary Examiner*—Ismael Izaguirre

(57) ABSTRACT

A hernia prosthesis deployment device includes an elongated rod through which a drawstring extends forming a loop at the distal end. The size of the loop is controlled by pulling on an end of the drawstring extending from the proximal end of the rod. A plurality of independent segments are threaded onto the drawstring loop in bead-like fashion, such that when the loop is expanded, the loop with segments is flexible. When the loop is contracted, the segments force the loop into a planar configuration. A surgical patch is attached to the loop such that it can be folded and pushed into position in the body. Thereafter, the loop is contracted by pulling the drawstring forcing the loop and attached patch into a planar configuration to cover the defect to be repaired.

18 Claims, 3 Drawing Sheets

US 6,575,988 B2

DEPLOYMENT APPARATUS FOR SUPPLE SURGICAL MATERIALS

FIELD OF THE INVENTION

The present invention relates to an apparatus for placing and deploying supple surgical materials such as surgical mesh within the body, and more particularly to a substantially planar surgical mesh prosthesis for bridging a hernia and an apparatus for placing and deploying the prosthesis.

BACKGROUND OF THE INVENTION

Modern surgical techniques are intended to be minimally invasive. Endoscopic surgery is a prime example of this minimally invasive approach and has led to the development of various instruments that may be inserted through a small incision to operate internally. In some circumstances, such as with specimen retrieval pouches or organ pouches and bags, the surgical instrument places, controls and/or deploys a supple material, e.g., a latex bag. The supple material may assume folded, expanded and contracted states, e.g., for inserting, opening and closing within the body. Accordingly, various apparatus have been devised to accomplish these transitions and functions relative to supple surgical materials like latex sheeting and textiles, but these apparatus are frequently complex, expensive and utilize exotic materials.

Minimally invasive procedures are also commonly employed in the treatment of hernias, e.g., in the placement of mesh surgical prostheses. Surgically implantable mesh patches for the repair of inguinal and other abdominal wall hernias are commonly used and provide tension-free repairs by bridging the hernia defect. Patches of this type constitute a structural support which decreases recurrence rates and because they do not require the displacement of tissues to cover the hernia, decrease postoperative discomfort. Frequently, prostheses of this type are sutured in place, i.e., proximate to the periphery of the patch. An alternative to suturing the prosthesis is to insert it into the properitoneal space. U.S. Pat. No. 5,916,225 to Kugel discloses a hernia prosthesis having a resilient ring made of synthetic material, such as nylon, polypropylene or polyester enclosed within a pocket formed by opposing planar segments of surgical mesh that are attached together to encapsulate the ring. A slit is provided in one of the planar segments to permit the surgeon to insert a finger therein in order to push the prosthesis through an incision in the abdominal wall into the properitoneal space and across the hernia. The resilient ring urges the pocket into a deployed planar configuration, i.e., to straighten the wrinkling and folding of the pocket that occurs in the course of its placement. The disadvantages associated with the device disclosed in U.S. Pat. No. 5,916,225 are that each layer of mesh is stiff and dense, such that the combination of two layers and the resilient ring constitutes a rigid, high mass prosthesis which tends to cause discomfort and resists conformance to the patient's anatomy. Further, the high mass prosthesis with resilient ring must be compressed into a stressed condition in order to be passed through the incision. Alternatively, the incision must be made large enough to pass the fully expanded prosthesis.

It is therefore an object of the present invention to provide a hernia repair prosthesis for use in a surgical hernia repair that has low mass, greater flexibility and that may be placed proximate to the site of the defect through a small incision in a stress free condition. More generally, it remains an objective to devise simple effective apparatus for positioning, deploying and controlling supple surgical material, such as a surgical mesh hernia prosthesis.

SUMMARY OF THE INVENTION

The problems and disadvantages associated with conventional supple surgical material deployment devices are overcome by the present invention which includes an elongated rod having a proximal end and a distal end. A drawstring with a first end and a second end runs along the length of the rod from the proximal end to the distal end and slidably passes through an opening at the distal end of the rod. The drawstring forms a loop at the distal end of the rod and the loop has a variable circumference varying between an expanded circumference and a reduced circumference, depending upon the position of said first end relative to said rod. A plurality of segments, each having a lumen therethrough, is threaded over the drawstring in the area of the loop. The segments bear against one another when the circumference of the loop is reduced and assume a relative alignment such that they are arranged to approximate a generally planar closed figure.

BRIEF DESCRIPTION OF THE FIGURES

For a better understanding of the present invention, reference is made to the following detailed description of several exemplary embodiments considered in conjunction with the accompanying drawings, in which.

DESCRIPTION OF THE PREFERRED EMBODIMENTS

Figure 1:
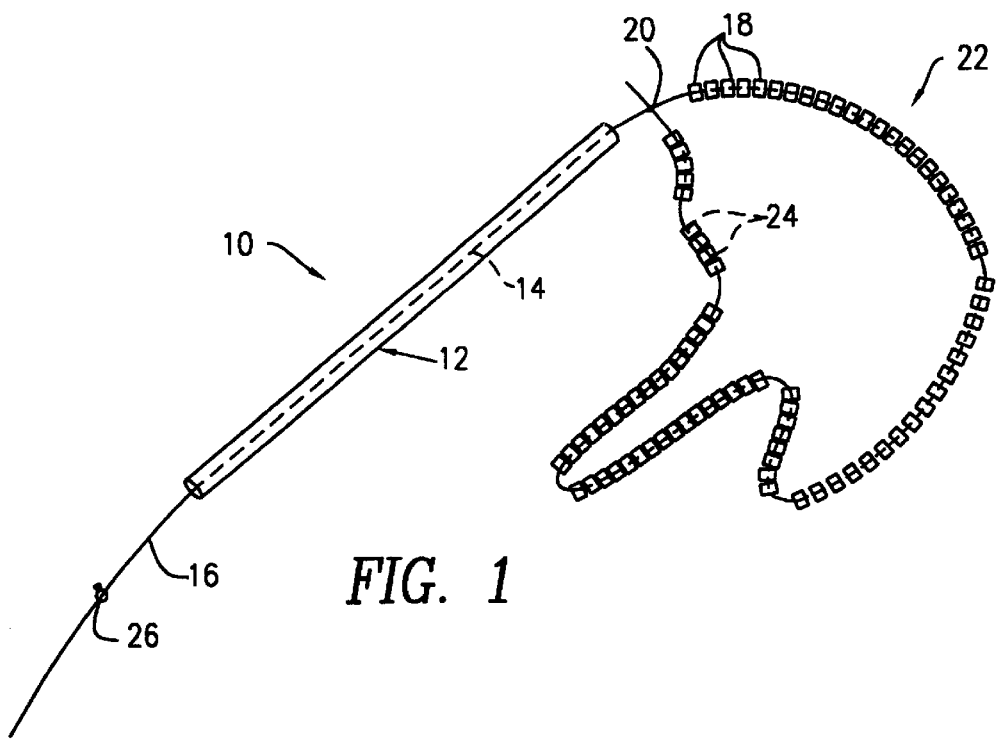
FIG. 1 is a plan view of a surgical material deployment apparatus in accordance with an exemplary embodiment of the present invention.
Figure 2:
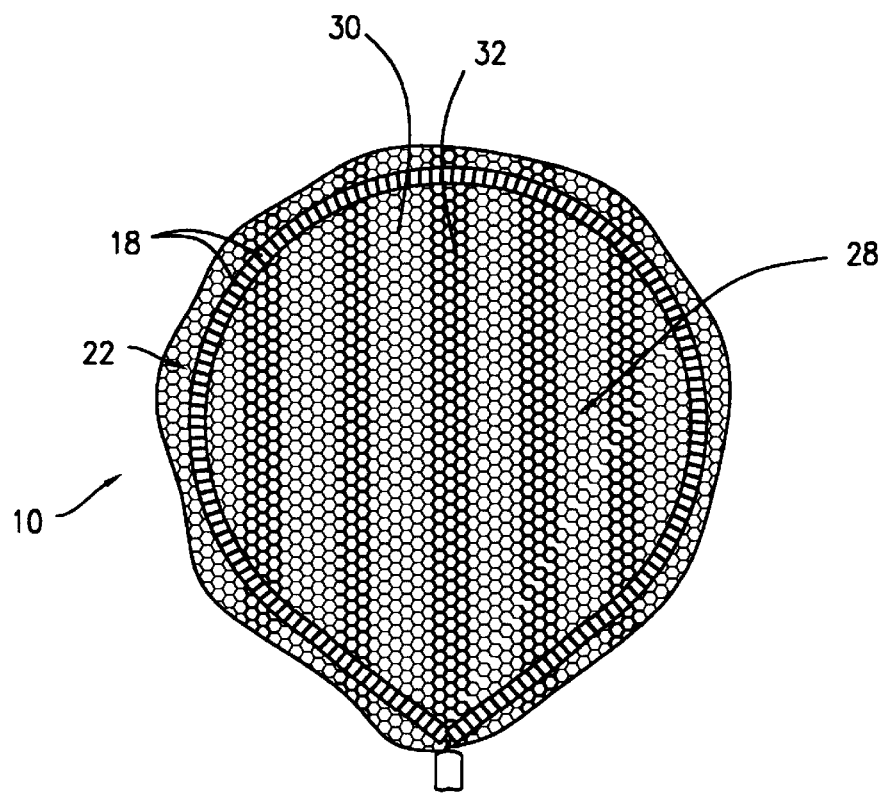
FIG. 2 is a plan view of the deployment apparatus of FIG. 1 in a deployed state and conjoined to a hernia repair prosthesis.

FIG. 1 shows a deployment apparatus 10 in accordance with the present invention having an elongated rod 12 with lumen 14 therein. The rod 12 may be grasped by the hand of a surgeon for positioning the deployment apparatus 10. A drawstring 16 extends through the lumen 14 of the rod 12, threads through a plurality of independent rigid, bead-like segments 18 then doubles back on itself to form a slipknot 20 to thereby define a loop 22 (combination of drawstring 16 and captured segments 18). The segments 18 are generally cylindrical as shown, but could be any other shape, such as, cubical or spherical, each having a lumen 24 therein through which the drawstring 16 may slidably pass. As a result, when the loop 22 has a greater length than the cumulative length of the segments placed end-to-end, the loop 22 is flexible. The slipknot 20 is preferably larger than the lumen 14, such that when the drawstring 16 is pulled in a proximal direction, the slipknot 20 encounters the rod 12 and the loop 22 is reduced in circumference. Accordingly, rod 12 functions as a segment/knot pusher and also as a handle for the apparatus 10. The loop 22 has a minimum circumference as determined by the cumulative length of the segments 18 as shown in FIG. 2, such that when the drawstring 16 is pulled taut, the segments 18 are inwardly radially compressed to configure the loop 22 into a rigid, composite, hoop-shaped structure. A limit knot 26 prevents the proximal end of the drawstring 16 from passing into the lumen 14 of the rod 12. The deployment apparatus 10 can therefore assume a relaxed state (loop 22 flexible) and a deployed state (loop 22 rigid). This capacity can be utilized to control the state of supple surgical material that is attached to the loop 22. For example, the loop 22 may be positioned about the neck of a specimen bag to allow it to be opened by causing the loop 22 to assume its rigid, hoop-shaped state.

FIG. 2 shows the deployment apparatus 10 of FIG. 1 after the drawstring 16 (see FIG. 1) has been pulled taut in a proximal direction. The segments 18 are pulled together as closely as possible, forcing the loop 22 with segments 18 into a generally circular configuration. A prosthesis (patch) 28 of surgical mesh material is attached to the loop 22 formed by the juxtaposed segments 18 and underlying drawstring 16. The prosthesis 28 may be formed from any biologically compatible, flexible, porous medical textile, such as those commonly used for reinforcing and occluding tissue defects. Knitted polypropylene monofilament mesh fabrics such as those available from Ethicon, Inc. under the Prolene, Vicryl and Panacryl trademarks may be utilized to fabricate the prosthesis 28. Other suitable mesh materials are available under the Marlex, Dacron, Teflon, Merselene and Polysorb (produced by United States Surgical Corporation) trademarks. Tissue regeneration may be induced through the use of absorbable materials in fabricating the prosthesis 28. It is preferred that the mesh used to form the prosthesis 28 be simultaneously flexible and have a low mass with a high porosity/open area ratio. These objectives are met by a material described in a copending application entitled KNITTED SURGICAL MESH, application Ser. No. 09/723,854 filed Nov. 28, 2000 and owned by the assignee of the present application, such application being incorporated herein by reference. The foregoing material is commercially available from Ethicon, Inc. under the trademark PROLENE*SOFT.

The prosthesis 28 preferably has visible alternating stripes 30, 32 or other indicia to aid in identifying the orientation of the prosthesis 28 when it is being placed in the body of the patient. While a circular prosthesis 28 may be used in certain circumstances, an oblong or rectangular shape, having a greater extent in one dimension may also be utilized. Accordingly, the stripes 30, 32 may be used to orient an elongated prosthesis 28 at the surgical site, e.g., by presenting a readily appreciable indicia of orientation. The stripes 30, 32 may be provided by utilizing a pattern of different color fibers in the textile from which the prosthesis 28 is made. Alternatively, stripes or other indicia may be printed on or otherwise applied to the prosthesis 28.

The prosthesis 28 may be attached to the loop 22 by stitching that interlocks to prevent the disassociation of the prosthesis 28 from the loop 22. Another method for attachment is to weave the drawstring 16 through the prosthesis 28 at spaced points along the periphery of the loop 22 and intermediate selected segments 18. Alternatively, the prosthesis 28 can be removably attached to the loop 22 by removable stitching, e.g., as shown below in FIG. 4. Removable attachment permits the loop 22 to be removed after placement of the prosthesis 28 at the hernia repair site. In this manner, the thickness and rigidity of the prosthesis 28 can be reduced. Alternatively, the segments 18 and drawstring 16 may be made from materials that can be absorbed by the body, such that the entire loop 22 with attached prosthesis 28 can be left at the hernia repair site, e.g., by snipping the drawstring between the limit knot 26 and the rod 12 and withdrawing the rod 12.

Figure 3:
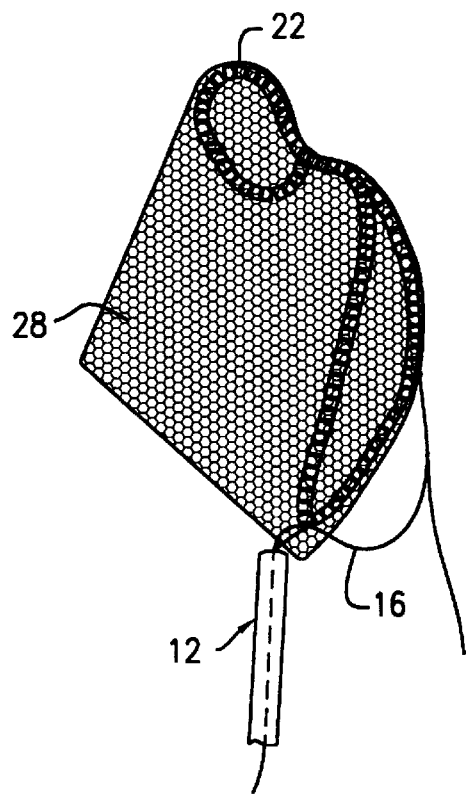
FIG. 3 is a perspective view of the deployment apparatus and prosthesis of FIG. 2 in a folded, undeployed state.

FIG. 3 shows the prosthesis 28 attached to the loop 22 prior to the tightening of the drawstring 16. When the drawstring 16 is in the untightened state, the loop 22 is free to assume various shapes, permitting the folding of the attached prosthesis 28. The prosthesis 28 can be folded prior to insertion into the surgical incision leading to the defect to be repaired, thereby reducing its size and permitting it to pass through a smaller incision. Once the prosthesis 28 is positioned proximate to the defect, the drawstring 16 can be pulled, forcing the segments 18 into the circular configuration shown in FIG. 2 and straightening the prosthesis 28 into a flattened configuration positioned across the defect.

Figure 4:
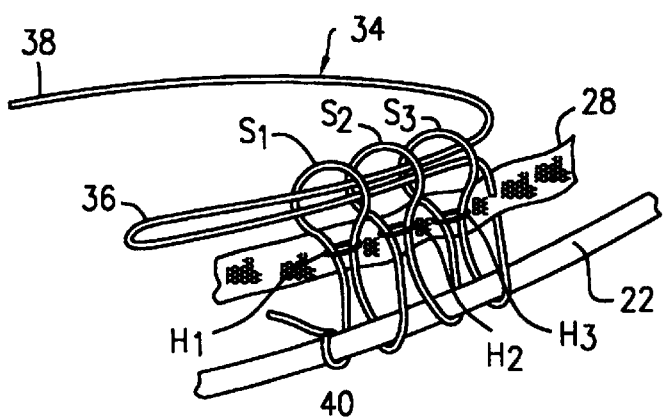
FIG. 4 is a diagrammatic, perspective view of a releasable stitching arrangement that may be employed to releasably attach a hernia prosthesis to the deployment apparatus of the present invention.

FIG. 4 shows one exemplary method of implementing a removable stitching arrangement to releasably retain the prosthesis 28 (only a portion of which is shown to simplify the illustration) in association with the loop 22. For simplicity of illustration, the loop 22 is shown as a solid elongated element rather than a composite of a plurality of segments 18 on a drawstring 16. More particularly, thread 38 is tied at knot 40 to the loop 22. The thread 38 passes under the loop 22 through a first hole $H_1$ in the prosthesis 28 to form a stitching loop $S_1$ back down through hole $H_1$, under and around loop 22, through hole $H_2$ to form stitching loop $S_2$, back down through hole $H_2$, and so forth to form stitching loop $S_3$. The thread 34 is then formed into an elongated release loop 36 which is passed through the stitching loops $S_1$, $S_2$, $S_3$, When the free end 38 of thread 34 is pulled, the release loop 36 is pulled through the stitching loops $S_1$, $S_2$, $S_3$, allowing them to be withdrawn from holes $H_1$, $H_2$, $H_3$ and permitting the prosthesis 28 to be disassociated from the loop 22. While only three releasable stitches, i.e., associated with $S_1$, $S_2$, and $S_3$ are shown, the same structures and principles of operation can be implemented around the entire periphery of the loop 22 to releasably secure the prosthesis 28 to the loop 22. In this manner, the loop 22 can be removed from the surgical site after placement of the prosthesis 28. The embodiment depicted in FIGS. 1–3 employs a slipknot 20 which can be either locking or non-locking, with the locking slipknot 20 being more appropriate for use in those instances when the loop 22 is left at the surgical site. Non-locking slipknots 20 facilitate removal of the loop 22, as described further below.

Figure 5:
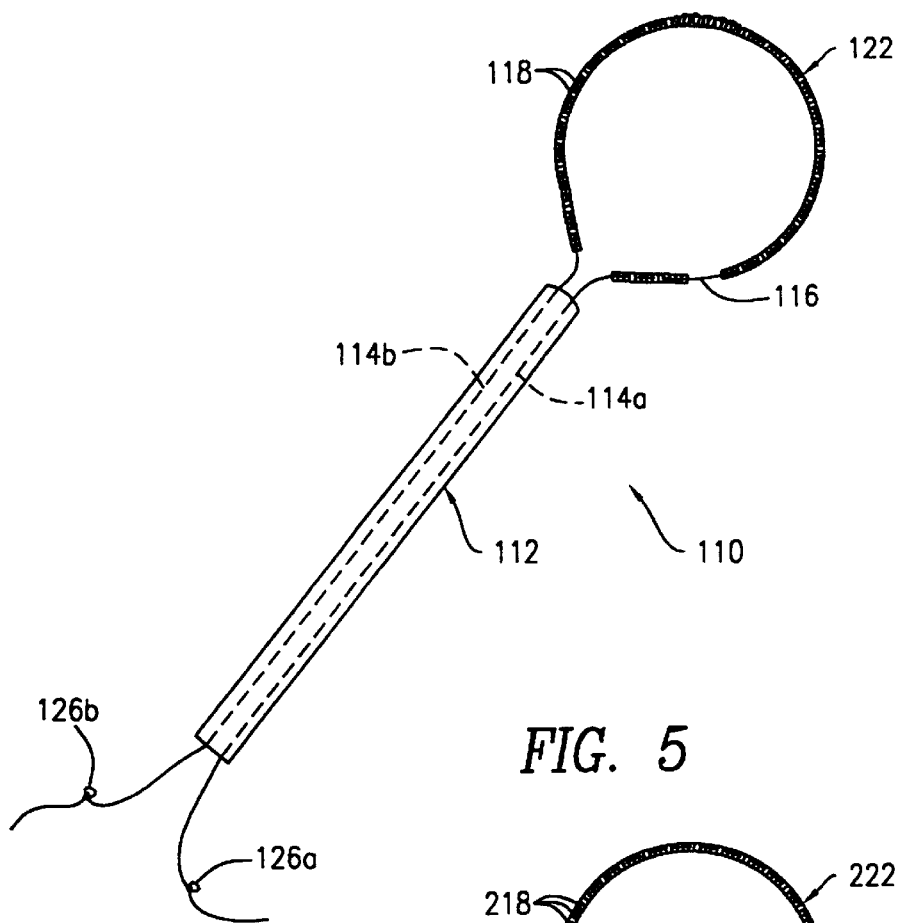
FIGS. 5 and 6 are diagrammatic views of second and third exemplary embodiments of the present invention, respectively.
Figure 6:
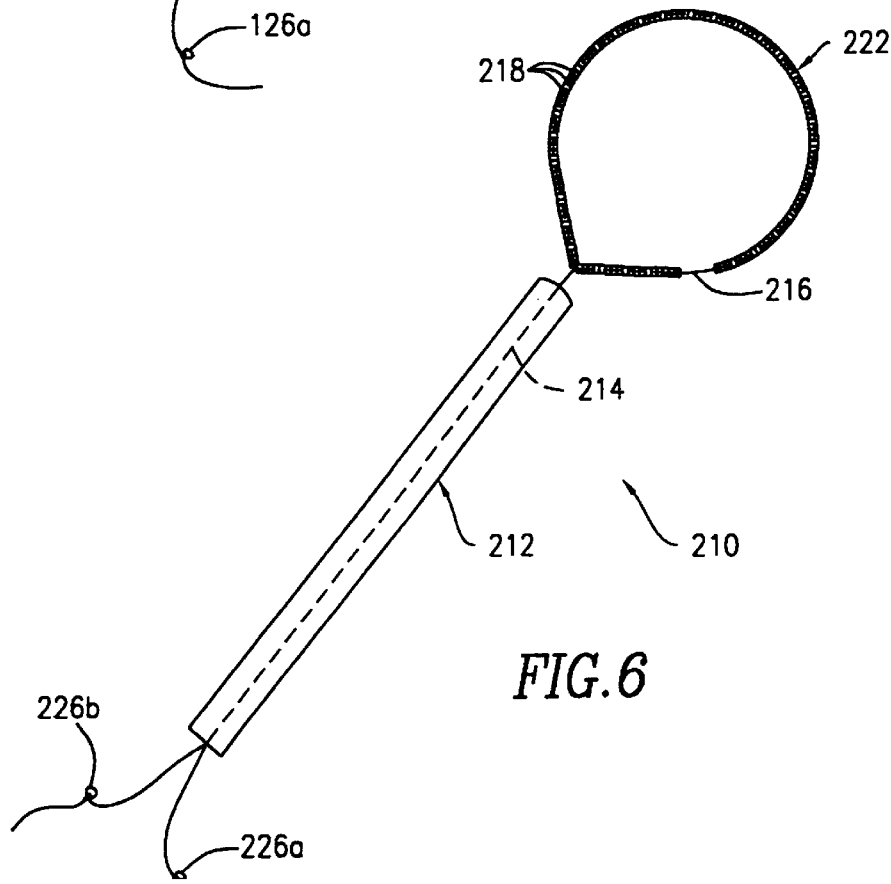

The prosthesis 10 may be used in the surgical repair of a hernia in accordance with the procedure described in U.S. Pat. No. 5,916,225 to Kugel, such patent being incorporated herein for its teaching relative to this procedure, which is also known in the art. Briefly, the repair of an inguinal hernia is made in accordance with this known procedure utilizing the present invention by inserting the prosthesis 28 attached to a folded loop 22 through a relatively small, oblique incision, e.g., 2 to 3 centimeters in length, made in the patient's abdomen above the internal ring location of the inguinal hernia. To prepare for insertion of the prosthesis, the surgeon performs a dissection through the oblique incision deep into the patient's pro-peritoneal space, using the muscle splitting technique. This dissection process results in a pocket in the pro-peritoneal space that can receive the prosthesis 28. The prosthesis 28 and loop 22 of the present invention can be then inserted into the cavity previously surgically formed in the pro-peritoneal space. After the prosthesis 28 and loop 22 are at the proper insertion depth, the drawstring 16 can be pulled taut to deploy the prosthesis 28 over the defect. After deployment, the drawstring 16 can be snipped to allow withdrawing the rod 12 and leaving the loop 22 and prosthesis 28 in place. Alternatively, the thread 34 attaching the prosthesis 28 to the loop 22 may be formed into releasable stitching, such that when a free end 38 of the thread 34 is pulled from a position outside the patient's body, the prosthesis 28 becomes disassociated from the loop 22, allowing the loop 22 to be withdrawn from the surgical site but leaving the prosthesis 28 in place covering the defect. When the loop 22 is withdrawn following placement, it is preferred that the loop 22 be free to loosen when tension exerted on the drawstring 16 by the surgeon is released, i.e., it is preferred that the slipknot 20 be of the non-locking type or that a device 110, 210 as shown in FIGS. 5 and 6 be employed. In this manner, the loop 22 will become limp, allowing it to conform to the confines of the incision and to be removed without causing any unnecessary stress to the incision.

FIG. 5 shows a deployment apparatus 110 like that of FIG. 1 but having a pair of lumens 114a and 114b. The elements of the embodiments shown in FIGS. 5 and 6 having similar form and function as those of the embodiment of FIGS. 1–3 have been designated by corresponding reference numerals increased by one hundred and two hundred, respectively. Instead of utilizing a slipknot for forming the loop 122, the loop 122 is formed by the passage of the drawstring 116 into two separate lumens 114a, 114b. A pair of limit knots 126a, 126b prevent the drawstring 116 from inadvertently slipping through the rod 112 and releasing the segments 118. The limit knots 126a, 126b also limit the expanded size of the loop 122.

FIG. 6 depicts yet another deployment apparatus 210 wherein both ends of the drawstring 216 pass through the lumen 214 to form the loop 222 and two limit knots 226a, 226b limit the expansion of the loop 222. It should be appreciated that the ends of the drawstring 116, 216 protruding from the proximal end of the rod 112, 212 in FIGS. 5 and 6 respectively, could be tied together to unify them and provide a common limit knot, or could both be tied to a single common drawstring.

It should be understood that the embodiments described herein are merely exemplary and that a person skilled in the art may make many variations and modifications without departing from the spirit and scope of the invention as defined in the appended claims. For example, the shape of the segments 18 may be varied such that they interact in a specific way to give the resultant loop 22 a specific shape, e.g., in the manner of a ball and socket or abutting angled facets. While the present invention has been explained in terms of its use in hernia repair, there are other applications for introducing and deploying a supple surgical material into the body, such as in using specimen retrieval bags. Accordingly, all such variations and modifications in form or use are intended to be included within the scope of the invention as defined in the appended claims.

I claim:

1. A deployment device for supple surgical material, comprising:
    an elongated rod having a proximal end and a distal end, a drawstring with a first end and a second end running along the length of said rod from said proximal end to said distal end and slidably passing through an opening at said distal end of said rod, said drawstring forming a loop at said distal end of said rod, said loop having a variable circumference varying between an expanded circumference and a reduced circumference, depending upon the position of said first end relative to said rod, a plurality of segments each having a lumen therethrough and threaded over said drawstring in the area of said loop, said segments bearing against one another when the circumference of said loop is reduced and assuming a relative alignment such that said plurality of segments are arranged to approximate a generally planar closed figure.

2. The device of claim 1, wherein said rod has a lumen extending from the proximal end to the distal end, said opening in the distal end communicating with said lumen and said drawstring passing through said lumen from said proximal end to said distal end.

3. The device of claim 2, further including a surgical mesh patch attached to said loop such that said patch substantially bridges said generally planar closed figure when the circumference of said loop is reduced.

4. The device of claim 3, wherein said patch is foldable when said loop is expanded.

5. The device of claim 4, wherein said patch has a peripheral shape and extent approximating said generally planar closed figure.

6. The device of claim 5, wherein said patch is attached to said loop by stitching.

7. The device of claim 6, wherein said stitching is removable to allow said patch to be selectively disassociated from said loop.

8. The device of claim 7, wherein said stitching includes a release loop of thread that permits said stitching to be removed by pulling on an end of said thread.

9. The device of claim 2, wherein said loop is formed in said drawstring by a slipknot, said slipknot having dimensions exceeding the size of said opening in said rod.

10. The device of claim 9, wherein said slipknot is locking.

11. The device of claim 9, wherein said slipknot is non-locking.

12. The device of claim 9, wherein said drawstring has a limit knot proximate said second end beyond said proximal end of said rod.

13. The device of claim 2, wherein said rod has a pair of lumens, a first accommodating said first end of said drawstring and a second accommodating said second end of said drawstring.

14. The device of claim 2, wherein said first end and said second end of said drawstring both extend through said lumen.

15. The device of claim 3, wherein said patch is made from a knitted polypropylene monofilament mesh material.

16. A prosthesis system, comprising:
    a surgical mesh patch;
    holding means for holding said patch for introduction through an incision for placement in a selected position in the body of a patient, said holding means having an elongated portion that may be manually grasped by a surgeon and a patch deployment portion capable of selectively assuming an expanded state wherein said patch is stretched flat and a contracted state wherein said patch is folded; and attaching means for releasably attaching said patch to said deployment portion, said attaching means extending from said patch to a position permitting a surgeon to grasp and control said attaching means when said patch has been placed in the selected position within the body of the patient.

17. The system of claim 16, further comprising limiting means for limiting said deployment portion to a preselected state of expansion.

18. The system of claim 16, further comprising locking means for locking said deployment portion in a selected state of expansion.

* * * * *